US012605348B2

(12) United States Patent　　　　　　(10) Patent No.:　US 12,605,348 B2

Lopez et al.　　　　　　　　　　　　　(45) Date of Patent:　Apr. 21, 2026

(54) PHARMACEUTICAL FORMULATIONS OF NAPROXEN FOR SOFT GEL ENCAPSULATION AND COMBINATIONS THEREOF

(71) Applicant: Catalent Ontario Limited, Windsor (CA)

(72) Inventors: John Lopez, Windsor (CA); Peter Draper, Amherstburg (CA); Sankalp Vashishtha, Mississauga (CA); Nancy Klassen, Windsor (CA); Christina Armstrong, Windsor (CA)

(73) Assignee: Catalent Ontario Limited, Windsor (CA)

( * ) Notice: Subject to any disclaimer, the term of this patent is extended or adjusted under 35 U.S.C. 154(b) by 0 days.

(21) Appl. No.: 18/400,069

(22) Filed: Dec. 29, 2023

(65) Prior Publication Data

US 2024/0139132 A1　　May 2, 2024

Related U.S. Application Data

(60) Continuation of application No. 16/583,903, filed on Sep. 26, 2019, now Pat. No. 11,896,566, which is a continuation of application No. 15/285,968, filed on Oct. 5, 2016, now Pat. No. 10,463,637, which is a division of application No. 13/574,159, filed as application No. PCT/CA2011/000059 on Jan. 29, 2011, now Pat. No. 9,480,667.

(30) Foreign Application Priority Data

Jan. 19, 2010　(CA) ..................................... 2690488

(51) Int. Cl.
　　A61K 31/192　　(2006.01)
　　A61K 9/00　　　(2006.01)
　　A61K 9/48　　　(2006.01)
　　A61K 45/06　　(2006.01)

(52) U.S. Cl.
　　CPC .......... *A61K 31/192* (2013.01); *A61K 9/0053* (2013.01); *A61K 9/48* (2013.01); *A61K 9/4833* (2013.01); *A61K 9/4858* (2013.01); *A61K 9/4866* (2013.01); *A61K 45/06* (2013.01)

(58) Field of Classification Search
　　None
　　See application file for complete search history.

(56) References Cited

U.S. PATENT DOCUMENTS

| | | | |
|---|---|---|---|
| 4,443,428 A | 4/1984 | Oshlack et al. | |
| 4,522,828 A | 6/1985 | Jeffery et al. | |
| 5,071,643 A | 12/1991 | Yu | |
| 5,073,371 A | 12/1991 | Turner et al. | |
| 5,360,615 A | 11/1994 | Yu et al. | |
| 5,484,606 A | 1/1996 | Dhabhar | |
| 5,641,512 A | 6/1997 | Cimiluca | |
| 6,387,400 B1 | 5/2002 | Tindal et al. | |
| 2001/0007668 A1 | 7/2001 | Sawyer | |
| 2007/0053868 A1 | 3/2007 | Chidambaram et al. | |
| 2008/0014274 A1 | 1/2008 | Bubnis | |
| 2009/0318558 A1 | 12/2009 | Kim et al. | |

FOREIGN PATENT DOCUMENTS

| | | | |
|---|---|---|---|
| CA | 2214399 A1 | 10/1996 | |
| CA | 2214399 C | 3/2001 | |
| CA | 2600023 A1 | 9/2006 | |
| CA | 2600023 C | 11/2011 | |
| EP | 0097523 A2 | 1/1984 | |
| EP | 2289493 A1 | 3/2011 | |
| JP | H01502185 A | 8/1989 | |
| JP | H08157355 A | 6/1996 | |
| JP | H09508128 A | 8/1997 | |
| JP | H11502838 A | 3/1999 | |
| JP | 2002509103 A | 3/2002 | |
| JP | 2006514119 A | 4/2006 | |
| WO | 9507103 A1 | 3/1995 | |
| WO | 9519759 A1 | 7/1995 | |
| WO | 9629997 A1 | 10/1996 | |
| WO | 2006096580 A1 | 9/2006 | |
| WO | 2007092784 A1 | 8/2007 | |

OTHER PUBLICATIONS

Extended European Search Report for European Application No. 11734283.2, mailed Mar. 27, 2014, 8 Pages.
International Preliminary Report on Patentability for International Application No. PCT/CA2011/000059, mailed Aug. 2, 2012, 8 Pages.
International Search Report for International Application No. PCT/CA2011/000059, mailed Mar. 31, 2011, 3 Pages.
Written Opinion for International Application No. PCT/CA2011/000059, mailed Mar. 31, 2011, 6 Pages.
Extended European International Search Report on EP Application No. 21177143.1-1109 dated Oct. 1, 2021, 11 pages.
Davidson R.L., "Handbook of Water-Soluble Gums and Resins," McGraw-Hill Book Company, 1980, 31 Pages.
Martha W., et al., "The Merck Index: an Encyclopedia of Chemicals, Drugs, and Biologicals," Merck and Co., Inc, 1983, 1 Page.
Norman F E., et al., "CTFA Cosmetic Ingredient Dictionary," The Cosmetic, Toiletry and Fragrance Association Inc, 1982, pp. 201-203.

*Primary Examiner* — Tigabu Kassa

(74) *Attorney, Agent, or Firm* — Lowenstein Sandler LLP

(57) ABSTRACT

Disclosed are methods of using a naproxen fill formulation suitable for encapsulation into a soft gel dosage unit to treat inflammation and pain. Methods include administering naproxen to a subject in need thereof to treat pain and inflammation. Methods can include administering naproxen together with another medicament to a subject in need thereof to treat an additional condition such as a cough, cold, allergy, congestion, etc.

20 Claims, No Drawings

PHARMACEUTICAL FORMULATIONS OF NAPROXEN FOR SOFT GEL ENCAPSULATION AND COMBINATIONS THEREOF

CROSS REFERENCE TO RELATED APPLICATIONS

This application is a Continuation of application Ser. No. 16/583,903, filed Sep. 26, 2019, which is a Continuation of U.S. Pat. No. 10,463,637, filed Oct. 5, 2016, which is a Divisional of U.S. Pat. No. 9,480,667, filed Sep. 21, 2012, which is a § 371 National Stage Application of PCT/ CA2011/000059, filed Jan. 19, 2011, which claims priority to Canadian Patent No. 2,690,488, filed Jan. 19, 2010.

FIELD OF THE INVENTION

The present invention generally relates to oral pharmaceutical formulations. More particularly, the invention relates to an improved pharmaceutical formulation of naproxen suitable for encapsulation into a soft gel capsule dosage form, and process of preparation thereof.

BACKGROUND OF THE INVENTION

Soft gel capsules have been widely known and used for many years and for a variety of purposes. Soft gel capsules are quite different from hard-shell capsules, in that they are formed, filled and sealed in a one step process from a plasticized shell material incorporating desired functional properties, and a wide range of liquid fill materials that may be hydrophilic, hydrophobic or combinations thereof. It is well known in the art to use soft gel capsules to contain materials for oral consumption, such as vitamins, nutritional supplements and active pharmaceutical ingredients that are specially formulated in liquid vehicles or carriers for soft gel encapsulation.

However, not all liquids can be used as the only vehicle or carrier in soft gel capsules. Liquids such as water, propylene glycol, glycerin, low molecular weight alcohols, ketones, acids, amines and esters can be used only with other liquids to prepare vehicles or carriers in soft gel capsules, known in the art as fill formulations. Such liquids may be used as functional components of soft gel fill material.

A limitation in the use of soft gel capsules is that it may not be possible to formulate the active pharmaceutical ingredient in a volume of solvent small enough to produce a soft gel capsule that delivers the desired dosage amount and is economically appropriate and comfortable to ingest by the patient. This limitation is particularly relevant when a clear solution or dispersion of the pharmaceutical agent is desired. One such pharmaceutical agent is naproxen, which is poorly soluble in water and has limited solubility in the combinations of ingredients typically used for soft gel capsule fill materials.

Naproxen is a non-steroidal anti-inflammatory drug (NSAID) that is commonly used to relieve pain and to treat inflammatory conditions. Naproxen, (+)-(S)-2-(6-methoxynaphthalen-2-yl) propanoic acid, is a member of the 2-arylpropionic acid (profen) family of NSAID's. Naproxen and other NSAID's are practically insoluble in water. The solubility of naproxen in liquids and combinations of liquids that are suitable vehicles or carriers in soft gel capsules is insufficient to provide a reasonably sized capsule. In particular, the solubility of naproxen in polyethylene glycol, the preferred vehicle or carrier for hydrophilic active ingredients, is insufficient to provide a reasonably sized capsule small enough to be comfortably administered to most patients.

Several processes have been developed in efforts to increase the solubility, and, hence, the bioavailability of naproxen. One such prior art process is disclosed by Yu et al. in U.S. Pat. Nos. 5,071,643 and 5,360,615, both of which disclose the use of a water-based solvent system for enhancing the solubility of an acidic pharmaceutical agent, such as naproxen, to produce a highly concentrated solution suitable for encapsulation in soft gel capsules. The solvent system disclosed includes 10% to 80% by weight polyethylene glycol, 1% to 20% by weight water and hydroxide ion species. The solvent systems provide for a highly concentrated solution capable of encapsulation into a small vessel, such as a soft gel capsule, to permit easy swallowing and to provide a pharmaceutically effective dose of a pharmaceutical agent, such as naproxen. The method disclosed in the Yu et al. references the formation of a solution of the pharmaceutical agent (naproxen) in a water-based solvent system utilizing a solubility-enhancing agent such as sodium hydroxide, ammonium hydroxide or potassium hydroxide to solubilize the naproxen by partial neutralization.

Tindal et al. discloses another prior art process in U.S. Pat. No. 6,387,400, for increasing the concentration of a pharmaceutically active ingredient for dosage units of soft gel capsules. This disclosure describes a process for ibuprofen and refers to other acidic compounds such as naproxen. The method disclosed by Tindal et al. is based on the preparation of a solution of the pharmaceutical agent in polyethylene glycol and a hydroxide ion source through a process based on the gradual and incremental addition of the pharmaceutical agent and the hydroxide ion source.

A further limitation to the use of certain liquids as vehicles or carriers for soft gels are is the pH value of the liquid as taught by Yu et. al., in U.S. Pat. No. 5,360,615. For example, the pH of the fill liquid should not be below 2.5 or above 7.5. At pH values below 2.5, the gelatin may be hydrolyzed causing leaking, whereas at pH's greater than 7.5, the gelatin is tanned resulting in decreased solubility of the gelatin shell.

Naproxen and naproxen sodium are recognized active pharmaceutical ingredients and the subject of monographs in the USP. Naproxen sodium is a recognized sodium salt form of naproxen. Although naproxen sodium is highly soluble in polyethylene glycol, the use of the more soluble naproxen sodium presents other problems. When naproxen sodium is solubilized in polyethylene glycol, the resulting solution is alkaline, which is corrosive to the soft gel shell. Thus, naproxen sodium is unsuitable for soft gel encapsulation.

The prior art teaches the use of polyethylene glycol and hydroxide ion source to solubilize pharmaceutical agents, such as naproxen and ibuprofen. However, the addition of a hydroxide ion source, such as sodium hydroxide, ammonium hydroxide or 15 potassium hydroxide, to neutralize the solution results in an increase in overall volume of the fill material. Increasing the concentrations of active ingredients, such as naproxen, naproxen sodium or other NSAID's, in soft gel dosage forms and/or units without necessitating an increase in overall volume of the fill material (and thereby increasing overall size of the dosage form) and/or without an increase disintegration or dispersion of the capsule shell have proven difficult to accomplish in the art.

As shown in the prior art, the ability to adjust the pH of fill formulations is problematic without additional process steps. The prior art teaches to neutralize the solution containing the active ingredient through numerous addition steps using a hydroxide ion source, such as sodium hydroxide, ammonium hydroxide or potassium hydroxide. The ability to adjust the pH values of fill formulations is particularly relevant to combinations of NSAID's, such as naproxen, and other active pharmaceutical ingredients, such as phenylephrine hydrochloride, doxylamine succinate and dextromethorphan hydrobromide, where the solubility or stability of the other active ingredient may be optimized by adjusting the pH of the fill formulation (or neutralizing the acidic/basic API).

It would be advantageous and desirable to provide pharmaceutical formulations of NSAID's, such as naproxen, for encapsulation in soft gels, which produces a solution that accommodates higher concentrations of the active ingredient than previously described without increasing the overall size of the dosage form. Such pharmaceutical formulations would permit a reduction in overall size of the dosage form. It is also desirable to provide pharmaceutical formulations of NSAID's, such as naproxen, based on polyethylene glycol to provide a reasonably sized capsule that is not corrosive to the soft capsule shell.

It would also be advantageous and desirable to have improved processes to produce pharmaceutical formulations of naproxen and other NSAID's having adjustable pH values without needing to neutralize the solution containing the active ingredient through numerous addition steps. The elimination of the neutralization process permits a more economical and controllable manufacturing process. Also, the elimination of a 10 corrosive or caustic adjuvant such as sodium hydroxide provides a much safer process for the workplace.

SUMMARY OF THE INVENTION

In accordance with an aspect of the present invention, there is provided a naproxen formulation comprising naproxen, naproxen sodium, polyethylene glycol, propylene glycol, povidone, and water for increasing the stability, concentration, and bioavailability of naproxen. There is also provided a pharmaceutical formulation comprising an acidic NSAID, a basic NSAID, polyethylene glycol, propylene glycol, povidone, and water for increasing the stability, concentration, and bioavailability of the NSAID.

In accordance with another aspect of the present invention, there is provided a naproxen dosage form that provides increased stability, concentration, and bioavailability of naproxen comprising a drug delivery vehicle and a formulation comprising naproxen, naproxen sodium, polyethylene glycol, propylene glycol, povidone, and water disposed within the drug delivery vehicle. There is also provided a dosage form that provides increased stability, concentration, and bioavailability of a NSAID comprising a drug delivery vehicle and a pharmaceutical formulation comprising an acidic NSAID, a basic NSAID, polyethylene glycol, propylene glycol, povidone, and water.

The invention discloses a manufacturing process for the soft gel fill formulation disposed within a drug delivery vehicle providing advantages over those previously described.

It is a further aspect of the present invention to produce a highly concentrated solution in order to manufacture as small a capsule as possible to facilitate consumer acceptance.

The invention further provides a formulation of optimal stability and with adjustable pH values suitable for supporting a fill composition compatible with other active ingredients that may be incorporated into the drug delivery vehicle, including soft gel caps.

DETAILED DESCRIPTION OF THE PREFERRED EMBODIMENTS

A naproxen formulation capable of supporting higher naproxen concentrations, having enhanced bioavailability and having improved adjustability of pH values is disclosed. The naproxen formulation generally includes a combination of naproxen and naproxen sodium. The formulation may also include naproxen and naproxen sodium in combination with other active pharmaceutical ingredients. The present invention is disclosed with specific reference to naproxen, but is also applicable to other NSAID's that may have both acid and salt forms. A simplified process for preparing the formulations of the present invention is also disclosed which avoids the need for utilizing a neutralization process and numerous addition steps of a hydroxide ion species.

The improved naproxen formulation generally includes polyethylene glycol (PEG), propylene glycol, povidone, water, naproxen and naproxen sodium. PEG, preferably but not limited to PEG 400, is commonly used as emulsifying and solubilizing agent. Povidone is commonly used as a dispersing and suspending agent. In the present invention, povidone is of a suitable viscosity grade, for example but not limited to K12. The amount of naproxen in the formulation ranges from about 2% to about 25% by weight with the corresponding amount of naproxen sodium in the formulation ranging from about 25% to about 2% by weight. The total amount of naproxen and naproxen sodium by weight in the formulation may depend on desired capsule size, but preferably range from about 22% to about 30% by weight. The amount of PEG in the formulation ranges from about 40% to about 70% by weight. The amount of propylene glycol in the formulation ranges from about 1% to about 5% by weight. The amount of povidone in the formulation ranges from about 1% to about 6% by weight. The amount of water in the formulation ranges from about 1% to about 10% by weight.

It is contemplated that the excipients of the formulation of the present invention can be used with combinations of acid and base forms of other NSAID's. Examples of other acidic NSAID's suitable for use in accordance with this invention include, but are not limited to, indomethacin (indomethacin sodium trihydrate), ibuprofen (ibuprofen sodium dihydrate) and diclofenac (diclofenac potassium). The amount of indomethacin in the formulation ranges from about 2% to about 30% by weight and the corresponding amount of indomethacin sodium trihydrate ranges from about 30% to about 2% by weight. The total amount of indomethacin and indomethacin sodium trihydrate in the formulation may depend on desired capsule size, but preferably range from about 22% to about 35% by weight. The amount of ibuprofen in the formulation ranges from about 2% to about 25% by weight and the corresponding amount of ibuprofen sodium dihydrate ranges from about 25% to about 2% by weight. The total amount of ibuprofen and ibuprofen sodium dihydrate in the formulation may depend on desired capsule size, but preferably range from about 22% to about 30% by weight. The amount of diclofenac in the formulation ranges from about 2% to about 30% by weight and the corresponding amount of diclofenac potassium ranges from about 30% to about 2% by weight. The total amount of diclofenac and diclofenac potassium in the formulation may depend on desired capsule size, but preferably range from about 22% to about 35% by weight It is contemplated that the formulation of the present invention encompasses formulations of acid and base forms of one active pharmaceutical ingredient in logical combination with other active pharmaceutical ingredients. Logical combinations of the naproxen formulation of the present invention with one or more other active pharmaceutical ingredients may be useful for the treatment of symptoms associated with minor aches and pains, coughs, colds or allergy. For example, the analgesic effects of naproxen in combination with phenylephrine hydrochloride, which is used as a decongestant, may be useful to provide relief of cold and flu symptoms. The amount of phenylephrine hydrochloride in the formulation may range from about 0.01% to about 1% by weight. Other active pharmaceutical ingredients in logical combination with the naproxen formulation of the present invention include doxylamine succinate and dextromethorphan hydrobromide. The amount of doxylamine succinate in the formulation may range from about 0.01% to about 1% by weight. The amount of dextromethorphan hydrobromide in the formulation may range from about 1% to about 2% by weight.

A further unique feature of the present formulation is that the pH of the fill formulation can be adjusted by varying the relative proportions of naproxen and naproxen sodium within a capsule. Accordingly, the pH of the fill formulation can be controlled or selected by adjusting the ratios of the acid and salt forms of naproxen. The ratio of naproxen to naproxen sodium may range from about 9:1 to about 3:7, preferably in a ratio from about 3:2 to 2:3, and most preferred in a ratio of about 1:1. The present formulation eliminates the need for additional process steps to adjust pH values of fill formulations. The pH of the naproxen fill formulation ranges from about 2 to about 8. The capability to adjust the pH of the naproxen formulation is important to ensure the compatibility of the fill material with the gel shell, which encapsulates the naproxen formulation. Also, the ability to adjust the pH of the fill formulation to optimize stability of other active ingredients may be of critical importance for formulations containing naproxen in combination with other active ingredients.

Soft gel capsules used for the treatment of cold and flu symptoms may contain naproxen in combination with one or more other active ingredients. A typical example of a combination is with phenylephrine hydrochloride; the preferred fill formulation pH for optimum stability of phenylephrine in soft gel fill formulation is in the range of about 4 to about 6.

The present invention describes an improved method of manufacture of a naproxen formulation for use in, for example, a soft gel capsule. A combination of naproxen and naproxen sodium is solubilized in PEG, preferably polyethylene glycol 400 (PEG 400), propylene glycol, povidone, water and optionally other adjuvants known in the art of soft gel encapsulation to produce a highly concentrated solution which is suitable for encapsulation into a drug delivery vehicle such as a soft gel capsule.

The naproxen formulation comprising naproxen and naproxen sodium is sufficiently soluble in a hydrophilic fill formulation based on polyethylene glycol to provide a reasonably sized capsule that is not corrosive to the soft capsule shell. Furthermore, the combination of naproxen and naproxen sodium produces a solution that accommodates higher concentrations of the active ingredient than previously described that is suitable for encapsulation in soft gel capsules, without needing to neutralize the solution containing the active ingredient through numerous addition steps as taught in the prior art. The elimination of the neutralization process of the prior art permits a more economical and controllable manufacturing process. Also, the elimination of a corrosive or caustic adjuvant taught in the prior art, such as sodium hydroxide, provides a much safer process for the workplace.

The disclosed process is simpler, faster and thus more suitable for pharmaceutical manufacture through the elimination of potential process variables and attendant control procedures and provides more concentrated solutions of the active ingredient than described in the prior art. Therefore, greater potential for consistency or reproducibility can be achieved, which are key requirements of pharmaceutical processes. The disclosed process is also suitable for formulations comprising acid and base forms of other NSAID's.

The naproxen formulation is first prepared by combining the selected PEG, such as PEG 400, with propylene glycol. The mixture is stirred and heated to an elevated temperature, preferably at least 60° C., more preferably between about 60° C. to about 75° C., and most preferably about 70° C. Then, the desired amounts of naproxen and naproxen sodium are added to the mixture in the ratios mentioned above. The resulting mixture is maintained at an elevated temperature and stirred continuously to ensure complete dissolution, typically at least about 45 minutes. Then, purified water and povidone are added to the mixture. The resulting mixture is maintained at an elevated temperature and stirred continuously to ensure complete dissolution, typically at least about 10 minutes. The solution is deaerated and then cooled to room temperature.

The naproxen dosage form according to the present invention includes a drug delivery vehicle and the naproxen formulation dissolved within the drug delivery vehicle. The drug delivery vehicle is a soft gel capsule which can be made by techniques known to those skilled in the art. The soft gel capsule is preferred to the conventional two-piece type capsule as the soft gel capsule does not require any additional sealing of the capsule halves as would be required with the liquid filled two-piece type capsule, and commensurately, is less prone to physical degradations and deliberate tampering or contamination. The unit doses of the soft gel unit range from 10 to 1000 mg naproxen per capsule, preferably 200, 250, 300, 350 and 400 mg per capsule. To facilitate patient acceptance, it is preferred that the final capsule size should be not greater than a 14 oblong (~900 mg fill material).

In developing the soft gel capsule naproxen dosage form according to the present invention, it must be recognized that the naproxen formulation must be compatible with the soft gel shell. The soft gel shell formulations can be adjusted by a person skilled in the art to accommodate the formulation of the present invention. In general, soft gel shell capsule formulations consist of a gelling agent or a combination of suitable gelling agents, and one or more ingredients that are added to plasticize the soft gel shell formulation to produce a capsule of suitable characteristics as required by design or by preference.

The soft gel shell formulation may be based on gelatin or other gelling agents or their combinations suitable soft gel encapsulation. The present invention is based on but not restricted to soft gel shell formulations based on gelatin. The formulation in manufacture of soft gel capsules for use with the naproxen formulation of the present invention may be based on pharmaceutical grade gelatin that may be hide or bone mammalian or other species such as fish. A common gelatin formulation is lime bone or hide gelatin with a bloom strength range of 150 to 250 with a preferred bloom of 175. The gelatin formulation used for soft gel encapsulation of the naproxen formulation of the present invention includes but is not limited to, gelatin in the range of approximately 35% to 48% and a plasticizer or plasticizers ranging in amount from 4% to 34%. Suitable plasticizers for use with the formulation of the present invention include, but are not limited to, glycerin, sorbitol, a non-crystallizing sorbitol solution, sorbitol-sorbitan 10 solutions, sorbitan anhydrides, mannitol, propylene glycol and PEG 200. When sorbitol alone is utilized as the plasticizer, the amount can range from, but is not limited to a range of 18% to 24%. A suitable plasticizer is a non-crystallizing sorbitol-sorbitan solution of composition of approximately 10% to 65% sorbitol, approximately 10% to 65% 1,4-sorbitan, and approximately 1% to 15% mannitol, all percentages are by weight.

The capsule formulations can also include other suitable additives such as preservatives and/or coloring agents that are utilized to stabilize the capsule and/or impart a specific characteristic such as color or look to the capsule. Pharmaceutically acceptable preservatives can include, for example, methyl and propyl parabens. Color may be imparted to the gelatin shell using FD&C and/or D&C dyes. Opacifiers, such as titanium dioxide and/or iron oxides, may be employed to color and/or render the capsule opaque.

Below are examples illustrating several soft gel capsule formulations along with several examples of naproxen formulations made in accordance with the present invention. The examples presented below are intended to illustrate particular embodiments of the invention and are not intended to limit the scope of the specification, including the claims, in any way.

EXAMPLES

Process of Preparing Naproxen Formulation

Example 1

PEG 400 and propylene glycol were combined. The mixture was stirred and heated to 70° C. Desired amounts of naproxen and naproxen sodium were added to the mixture.

deaerated and then cooled to room temperature. A clear solution was formed with no visible suspended particles.

Naproxen Soft Gel Capsule Fill Formulations—Per Soft Gel Capsule

Example 2

| Ingredient | mg | % | |
|---|---|---|---|
| PEG 400 | 500 | 64.5 | |
| Propylene Glycol | 15 | 1.9 | |
| Povidone K12 | 35 | 4.5 | |
| Naproxen Sodium | 105 | 13.5 | (95.5 mg naproxen) |
| Naproxen | 105 | 13.5 | |
| Water | 15 | 1.9 | |
| Fill Weight | 775 | 100.0 | (10.84 minim) |

Example 3

| Ingredient | mg | % | |
|---|---|---|---|
| PEG 400 | 502 | 64.4 | |
| Propylene Glycol | 16 | 2.1 | |
| Povidone K12 | 36 | 4.6 | |
| Naproxen Sodium | 105 | 13.5 | (95.5 mg naproxen) |
| Naproxen | 105 | 13.5 | |
| Water | 16 | 2.1 | |
| Fill Weight | 780 | 100.0 | (10.91 minim) |

Ratio of Naproxen to Naproxen Sodium and Fill Material pH

Example 4

To illustrate how the pH of the fill material can be adjusted, formulations having various ratios of naproxen and naproxen sodium are demonstrated in the table below.

| | Ratio Naproxen:Naproxen Sodium | | | | | | |
|---|---|---|---|---|---|---|---|
| | 90 | 80 | 70 | 60 | 50 | 40 | 30 |
| | 10 | 20 | 30 | 40 | 50 | 60 | 70 |
| pH | 5.79 | 5.99 | 6.6 | 7.09 | 7.29 | 7.5 | 7.9 |
| | % Composition of Soft Gel Fill Material | | | | | | |
| PEG 400 | 65.03 | 64.86 | 64.69 | 64.52 | 64.36 | 64.19 | 64.03 |
| Propylene Glycol | 2.07 | 2.07 | 2.06 | 2.06 | 2.05 | 2.05 | 2.04 |
| Povidone K12 | 4.66 | 4.65 | 4.64 | 4.63 | 4.62 | 4.60 | 4.59 |
| Naproxen Sodium | 2.85 | 5.68 | 8.51 | 11.31 | 13.46 | 16.24 | 19.13 |
| Naproxen | 23.32 | 20.67 | 18.04 | 15.42 | 13.46 | 10.87 | 8.16 |
| Water | 2.07 | 2.07 | 2.06 | 2.06 | 2.05 | 2.05 | 2.04 |
| Total % | 100 | 100 | 100 | 100 | 100 | 100 | 100 |

The resulting mixture was stirred continuously for 45 minutes at 70° C. until the 10 naproxen and naproxen sodium were completely dissolved. Then, purified water and povidone were added to the mixture. The mixture was stirred continuously for 10 minutes at 70° C. The solution was

Naproxen Formulations with Additional Active Pharmaceutical Ingredients

The following examples are provided to illustrate the naproxen formulations of the present invention in combination with additional active pharmaceutical ingredients.

Example 5

| Ingredient | mg | % | |
|---|---|---|---|
| PEG 400 | 504 | 63.4 | |
| Propylene Glycol | 17 | 2.1 | |
| Povidone K12 | 38 | 4.8 | |
| Naproxen Sodium | 44 | 5.5 | (40 mg naproxen) |
| Naproxen | 160 | 20.1 | |
| Phenylephrine Hydrochloride | 5 | 0.6 | |
| Dextromethorphan HBr | 10 | 1.3 | |
| Water | 17 | 2.1 | |
| Fill Weight | 795 | 100.0 | (11.12 minim) |

Example 6

| Ingredient | mg | % | |
|---|---|---|---|
| PEG 400 | 504 | 62.6 | |
| Propylene Glycol | 17 | 2.1 | |
| Povidone K12 | 38 | 4.7 | |
| Naproxen Sodium | 44 | 5.5 | (40 mg naproxen) |
| Naproxen | 160 | 19.9 | |
| Phenylephrine Hydrochloride | 5 | 0.6 | |
| Dextromethorphan HBr | 10 | 1.2 | |
| Doxylamine Succinate | 6.25 | 0.8 | |
| Water | 19 | 2.4 | |
| Fill Weight | 805.25 | 100.0 | (11.27 minim) |

Comparative Data

Example 7

To illustrate how the formulation of the present invention reduces fill weight, a comparison between a commercial formulation of naproxen (Aleve) and a product of the present invention is provided below. The table below shows that for the same amount of naproxen per capsule, the product of the present invention provides reduced excipient fills weight. Thus, naproxen in accordance with the present invention could be administered in a smaller capsule size than the commercial product. Additionally, a larger amount of naproxen could be administered without increasing the capsule size of the commercial product.

| | Nominal Capsule | | | |
|---|---|---|---|---|
| | Total Weight/g | Fill Weight/g | Naprox-en/g | Naproxen % |
| Commercial Product (Aleve) | 1.31 | 0.96 | 0.2 | 20.8 |
| Product of the Present Invention | 1.15 | 0.84 | 0.2 | 23.8 |

Stability Profile of the Naproxen Soft Gel Capsule

The stability of a naproxen soft gel capsule containing the formulation described in Example 3 was determined using the rotating paddle dissolution apparatus of the USP. Samples of naproxen soft gel capsules were tested following storage at room temperature and under accelerating conditions for the intervals and packaging configurations as described in the following tables. All samples tested demonstrated rapid and essentially complete dissolution of the API. The examples below demonstrate that the formulation of the present invention is stable over 9 months.

Example 8

Lot PDS-1719 Stability Data—Specification NLT 75% (Q) in 45 minutes
Room temperature Conditions: 25° C./60% RH

| PDS-1719 | 0 | 3 Months | 6 Months | 9 Months |
|---|---|---|---|---|
| DISSOLUTION (80 Count) | 98.2% | 100.8% | 98% | 97% |
| DISSOLUTION (20 Count) | 98.2% | 100.6% | 99% | 97% |

Accelerated Conditions: 40° C./75% RH

| PDS-1719 | 0 | 1 Month | 2 Months | 3 Months |
|---|---|---|---|---|
| DISSOLUTION (80 Count) | 98.2% | 98.2% | 98.3% | 100.6% |
| DISSOLUTION (20 Count) | 98.2% | 98.4% | 98.1% | 101.5% |

Bulk Carton: 15-30° C./<65% RH

| PDS-1719 | 0 | 3 Months | 6 Months |
|---|---|---|---|
| DISSOLUTION (Bulk Carton) | 98.2% | 98.6% | 98.4% |

Example 9

Lot PDS-1720 Stability Data—Specification NLT 75% (Q) in 45 minutes
Room temperature Conditions: 25° C./60% RH

| PDS-1720 | 0 | 3 Months | 6 Months | 9 Months |
|---|---|---|---|---|
| DISSOLUTION (80 Count) | 100.2% | 103.3% | 100% | 99% |
| DISSOLUTION (20 Count) | 100.2% | 102.5% | 101.0% | 99% |

Accelerated Conditions: 40° C./75% RH

| PDS-1720 | 0 | 1 Month | 2 Months | 3 Months |
|---|---|---|---|---|
| DISSOLUTION (80 Count) | 100.2% | 100.5% | 100.4% | 103.1% |
| DISSOLUTION (20 Count) | 100.2% | 100.1% | 100.8% | 103.2% |

Bulk Carton: 15-30° C./<65% RH

| PDS-1720 | 0 | 3 Months | 6 Months |
|---|---|---|---|
| DISSOLUTION (Bulk Carton) | 100.2% | 100% | 100.5% |

In view of the teachings presented herein, other modifications and variations of the present inventions will be readily apparent to those of skill in the art. The foregoing discussion and description are illustrative of some embodiments of the present invention, but are not meant to be limitations on the practice thereof. Accordingly, all suitable modifications, variations and equivalents may be resorted to, and such modifications, variations and equivalents are intended to fall within the scope of the invention as described and within the scope of the claims.

What is claimed is:

1. A method of treating pain, inflammation or a combination thereof, comprising:

administering to a subject in need thereof, a pharmaceutical composition consisting essentially of:

about 2% to about 25% of naproxen;

about 25% to about 2% of naproxen sodium, wherein the weight ratio of naproxen to naproxen sodium is about 9:1 to about 3:7;

about 40% to about 70% polyethylene glycol;

about 1% to about 5% propylene glycol;

about 1% to about 6% povidone;

about 1% to about 10% water, wherein the total amount of naproxen and naproxen sodium ranges from about 22% to about 30% by weight of the total composition, wherein the pharmaceutical composition is free of a neutralizing agent, and wherein a volume of the fill formulation is less than a volume of a neutralized naproxen fill composition containing an equivalent dose of naproxen and naproxen sodium.

2. The method of claim 1, wherein the polyethylene glycol is PEG 400.

3. The method of claim 1, wherein the povidone is povidone K12.

4. The method of claim 1, wherein the pH of the composition ranges from about 2 to about 8.

5. The method of claim 1, further comprising administering an additional active pharmaceutical ingredient.

6. The method of claim 5, wherein the additional active pharmaceutical ingredient comprises phenylephrine hydrochloride.

7. The method of claim 6, wherein the phenylephrine hydrochloride is present in a pharmaceutical composition in an amount of about 0.01% to about 1% by weight based on the total weight of the pharmaceutical composition.

8. The method claim 7, wherein the pH of the pharmaceutical composition is about 4 to 6.

9. The method of claim 1, wherein the ratio of naproxen to naproxen sodium is about 9:1 to about 3:7.

10. The method of claim 1, wherein the ratio of naproxen to naproxen sodium is about 3:2 to about 2:3.

11. The method of claim 1, wherein the ratio of naproxen to naproxen sodium is about 1:1.

12. The method of claim 1, wherein the pharmaceutical composition is comprised in a drug delivery vehicle.

13. The method of claim 1, wherein the pharmaceutical composition is comprised in a soft gel capsule.

14. The method of claim 1, wherein the pharmaceutical composition is free of hydroxide ion.

15. The method of claim 1, wherein the pharmaceutical composition comprises a mass of not greater than about 900 mg.

16. A method of treating pain, inflammation or a combination thereof, and cough, cold, allergy, congestion or combinations thereof, comprising:

administering to a subject in need thereof, a pharmaceutical composition consisting essentially of:

about 2% to about 25% of naproxen;

about 25% to about 2% of naproxen sodium, wherein the weight ratio of naproxen to naproxen sodium is about 9:1 to about 3:7;

about 40% to about 70% polyethylene glycol;

about 1% to about 5% propylene glycol;

about 1% to about 6% povidone;

about 1% to about 10% water, wherein the total amount of naproxen and naproxen sodium ranges from about 22% to about 30% by weight of the total composition, wherein the pharmaceutical composition is free of a neutralizing agent, and wherein a volume of the fill formulation is less than a volume of a neutralized naproxen fill composition containing an equivalent dose of naproxen and naproxen sodium.

17. The method of claim 16, wherein the pharmaceutical composition further comprises phenylephrine hydrochloride, doxylamine succinate, dextromethorphan hydrobromide, or combinations thereof.

18. The method of claim 16, wherein the pharmaceutical composition comprises about 0.01% to about 1.0% by weight of phenylephrine hydrochloride.

19. The method of claim 16, wherein the pharmaceutical composition comprises about 0.01% to about 1% by weight of doxylamine succinate.

20. The method of claim 16, wherein the pharmaceutical composition comprises about 1% to about 2% by weight of dextromethorphan hydrobromide.

* * * * *